(12) United States Patent
Yamanashi

(10) Patent No.: US 9,953,237 B2
(45) Date of Patent: Apr. 24, 2018

(54) GLOSS DETERMINATION DEVICE AND GLOSS DETERMINATION METHOD

(71) Applicant: Panasonic Intellectual Property Management Co., Ltd., Osaka (JP)

(72) Inventor: Tomofumi Yamanashi, Kanagawa (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 260 days.

(21) Appl. No.: 14/860,069

(22) Filed: Sep. 21, 2015

(65) Prior Publication Data
US 2016/0098614 A1 Apr. 7, 2016

(30) Foreign Application Priority Data
Oct. 6, 2014 (JP) .................................. 2014-205645

(51) Int. Cl.
G06K 9/46 (2006.01)
H04N 5/225 (2006.01)

(52) U.S. Cl.
CPC ......... *G06K 9/4661* (2013.01); *H04N 5/2256* (2013.01); *G06K 2009/4666* (2013.01)

(58) Field of Classification Search
CPC .................... G06K 9/4661; H04N 5/2256
See application file for complete search history.

(56) References Cited

U.S. PATENT DOCUMENTS

| | | | | |
|---|---|---|---|---|
| 5,552,890 A * | 9/1996 | Nanna | ................... | G01N 21/57 101/211 |
| 7,127,280 B2 * | 10/2006 | Dauga | ................. | A61B 5/0059 356/369 |
| 7,679,747 B2 * | 3/2010 | Kuwada | ................. | G01N 21/57 356/445 |
| 7,974,467 B2 * | 7/2011 | Kaku | ................... | H04N 1/3878 382/167 |
| 2005/0271295 A1 | 12/2005 | Tabata et al. | | |

(Continued)

FOREIGN PATENT DOCUMENTS

JP 5-066381 A 3/1993
JP 2004-215991 8/2004
(Continued)

*Primary Examiner* — Neil Mikeska
(74) *Attorney, Agent, or Firm* — Greenblum & Bernstein, P.L.C.

(57) ABSTRACT

A gloss determination device includes: an image acquiring unit that acquires a parallelly polarized image obtained by photographing an object illuminated by first polarized light through a polarizing filter which passes a polarized component polarized in a same direction as a polarization direction of the first polarized light, and a perpendicularly polarized image obtained by photographing the object illuminated by second polarized light through a polarizing filter which passes a polarized component polarized in a perpendicular direction to the polarization direction of the second polarized light; a differential image producing unit that produces a differential image indicating differences in brightness between the parallelly polarized image and the perpendicularly polarized image; and a gloss determining unit that determines a gloss condition of the object based on the differential image.

7 Claims, 8 Drawing Sheets

(56) References Cited

U.S. PATENT DOCUMENTS

| | | | | |
|---|---|---|---|---|
| 2010/0283883 A1* | 11/2010 | Sato | .................... | G02B 27/283 348/335 |
| 2011/0304705 A1* | 12/2011 | Kantor | ................ | A61B 5/0059 348/49 |
| 2012/0327415 A1* | 12/2012 | Ito | .......................... | G01N 21/21 356/369 |
| 2013/0272585 A1* | 10/2013 | Mueller | ............... | G06K 9/0004 382/124 |
| 2014/0233810 A1* | 8/2014 | Spence | ............. | G06K 9/00013 382/115 |
| 2014/0285812 A1* | 9/2014 | Levitz | ................. | A61B 5/0066 356/479 |
| 2015/0256733 A1* | 9/2015 | Kanamori | ............ | H04N 5/2354 348/234 |
| 2015/0374309 A1* | 12/2015 | Farkas | .................. | G01N 21/21 600/473 |
| 2016/0135730 A1* | 5/2016 | Arai | ....................... | A61B 5/444 600/306 |

FOREIGN PATENT DOCUMENTS

| | | |
|---|---|---|
| JP | 2005-327009 | 11/2005 |
| JP | 2010-273737 | 12/2010 |
| WO | 2014/119257 A1 | 8/2014 |

\* cited by examiner

GLOSS DETERMINATION DEVICE AND GLOSS DETERMINATION METHOD

BACKGROUND

1. Technical Field

The present disclosure relates to a gloss determination device and a gloss determination method for determining a gloss condition of a human face or the like.

2. Description of the Related Art

Gloss sometimes appears on a surface of a substance due to balance between the state of the surface and the illumination condition. Strong gloss on a human face is called "shine".

In a case, for example, of determining a skin condition such as presence of wrinkles from a photographed image of a human face, the determination accuracy sometimes reduces unless influences of the gloss are considered. On the other hand, it is possible to determine a skin condition such as a sebum level from gloss appearing on the skin. Accordingly, it is beneficial for performing the skin condition determination or the like to determine conditions of gloss such as strength of gloss or distribution of gloss (hereinafter referred to as "gloss conditions").

Therefore, some techniques for determining the gloss conditions of an object are disclosed in PTL 1 to PTL 3 of the Patent Literatures.

In the technique disclosed in PTL 1, brightness of each pixel is calculated in a photographed image of a substance which is an object to be determined as to its gloss condition (hereinafter referred to as an "object"). In this technique disclosed in PTL 1, a region which has a much higher brightness than major components around the region is determined as a region which has a high gloss level (hereinafter referred to as a "gloss region").

In the technique disclosed in PTL 2, it is determined that a photographed image of an object contains a gloss region if pixels each having a brightness value equal to or larger than a predetermined threshold value are contained in the image.

In the technique disclosed in PTL 3, a total reflectivity and a quarter value diffuse reflectivity on a surface of an object are measured, where the total reflectivity is a reflectivity of light when natural light enters the surface of the object, and the quarter value diffuse reflectivity is a reflectivity of S polarized component of light when P polarized light enters the surface of the object. Then, in the technique disclosed in PTL 3, strength of gloss is determined based on a value obtained by subtracting a value which is four times as large as the quarter diffuse reflectivity from the total reflectivity.

CITATION LIST

Patent Literatures

PTL 1: Unexamined Japanese Patent Publication No. 2005-327009

PTL 2: Unexamined Japanese Patent Publication No. 2010-273737

PTL 3: Unexamined Japanese Patent Publication No. 2004-215991

However, according to the techniques disclosed in PTL 1 and PTL 2, it is difficult to accurately determine a gloss region in a case of an object having a bright surface as the skin of the white race. Also, according to the technique disclosed in PTL 3, the incident direction of the P polarized light must be set depending on the direction of the surface of the object, which is troublesome. In particular, according to the technique disclosed in PTL 3, reflectivity of an object like a human face, that has a surface containing parts which face toward different directions from one another, must be measured by changing the incident direction of the P polarized light part by part, so that huge effort and time are required. In view of the above, it is demanded to easily and accurately determine a gloss condition of an object.

SUMMARY

Thus, a non-limiting exemplary embodiment of the present disclosure provides a gloss determination device that is capable of easily and accurately determining a gloss condition of an object, and a gloss determination method that is capable of easily and accurately determining a gloss condition of an object.

In one general aspect, the techniques disclosed here feature a gloss determination device comprising: an image acquiring unit that acquires a parallelly polarized image obtained by photographing an object illuminated by first polarized light through a polarizing filter which passes a polarized component polarized in a same direction as a polarization direction of the first polarized light and a perpendicularly polarized image obtained by photographing the object illuminated by second polarized light through a polarizing filter which passes a polarized component polarized in a perpendicular direction to the polarization direction of the second polarized light; a differential image producing unit that produces a differential image indicating differences in brightness between the parallelly polarized image and the perpendicularly polarized image; and a gloss determining unit that determines a gloss condition of the object based on the differential image.

Additional benefits and advantages of the disclosed embodiments will be apparent from the specification and Figures. The benefits and/or advantages may be individually provided by the various embodiments and features of the specification and drawings, and need not all be provided in order to obtain one or more of the same.

These general and specific aspects may be implemented using a device, a system, a method, and a computer program, and any combination of devices, systems, methods, and computer programs.

According to the present disclosure, a gloss condition of an object can be easily and accurately determined.

DETAILED DESCRIPTION

Hereinafter, an exemplary embodiment of the present disclosure will be described with reference to the accompanying drawings. The present exemplary embodiment is an exemplary case of applying a gloss determination device according to the present disclosure to a device that determines a skin condition of a user's face.

Appearance and Usage State

Figure 1:
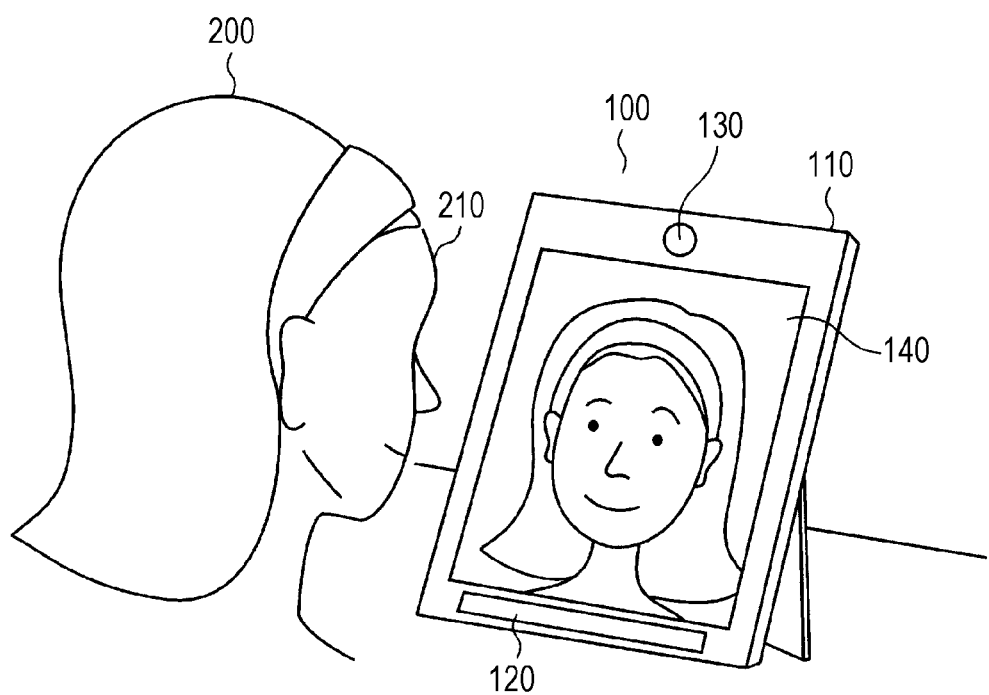
FIG. 1 illustrates an example of use of a gloss determination device according to an exemplary embodiment.

FIG. 1 is a diagram illustrating an appearance and an example of usage state of gloss determination device 100 according to an exemplary embodiment of the present disclosure.

As shown in FIG. 1, gloss determination device 100 is, for example, a tablet terminal which can be set upright on a desk. Gloss determination device 100 includes plate-like chassis 110 with a main surface, and light 120 with a polarizing filter, camera 130 with a polarizing filter, and display 140 with a touch panel. Light 120, camera 130 and display 140 are disposed on the main surface of chassis 110. User 200 uses gloss determination device 100 by adjusting the position of display 140 with a touch panel and her/his position so that face 210 is in a specified position such as a position facing display 140 with a touch panel at a distance of several tens of centimeters.

Light 120 with a polarizing filter has, for example, a light emitting unit in which a plurality of light emitting diodes (LEDs) are mounted, and a polarizing filter which passes a horizontally polarized light component. In the state that face 210 is in the above-mentioned specified position, light 120 with a polarizing filter illuminates face 210 by polarized light which is polarized in the horizontal direction (hereinafter simply referred to as "polarized light"). The polarizing filter may be removable.

Camera 130 with a polarizing filter has, for example, a digital camera, and a rotation angle adjustable polarizing filter. In the state that face 210 is in the above-mentioned specified position, camera 130 with a polarizing filter photographs face 210. The polarizing filter is capable of switching between a mode of passing a horizontally polarized component and a mode of passing a vertically polarized component. In other words, camera 130 with a polarizing filter is capable of photographing an object through a polarizing filter that passes a light component polarized in the horizontal direction, and is also capable of photographing the object through a polarizing filter that passes a light component polarized in a vertical direction. The polarizing filter may be removable.

Display 140 with a touch panel has, for example, a liquid crystal display that is slightly larger in size than the human face. Display 140 with a touch panel receives operations from user 200, and displays information for user 200.

Reflection of light on a surface of a substance is classified into specular reflection (surface reflection) and diffuse reflection (internal reflection). Gloss appearing on the surface of the substance is caused mainly by the specular reflection on the surface.

When polarized light enters a surface of a substance, its polarization property is maintained in the case of specular reflection, but is not maintained in the case of diffuse reflection. Therefore, it is possible to determine whether light from a surface of a substance is mainly caused by specular reflection or mainly caused by diffuse reflection according to whether or not polarization property of the polarized light is maintained.

Accordingly, gloss determination device 100 uses camera 130 with a polarization filter to extract, from reflected light, a brightness value of a component which is polarized in the same direction as the polarization direction of the polarized light and a brightness value of a component which is polarized in a perpendicular direction to the polarization direction of the polarized light. Then, gloss determination device 100 determines a part where a difference between the extracted brightness values is large as a part where the degree of specular reflection is high, or the degree of gloss on the surface of the substance is high.

In the present exemplary embodiment, the expression "the polarization direction is the same" includes not only exactly the same polarization direction, but also a polarization direction that is different from exactly the same polarization direction by an angle smaller than 45 degrees. Also, the expression "the polarization direction is perpendicular" includes not only the exactly perpendicular polarization direction, but also a polarization direction that is different from the exactly perpendicular direction by an angle smaller than 45 degrees.

Configuration of Device

Next, a configuration of gloss determination device 100 will be described.

Figure 2:
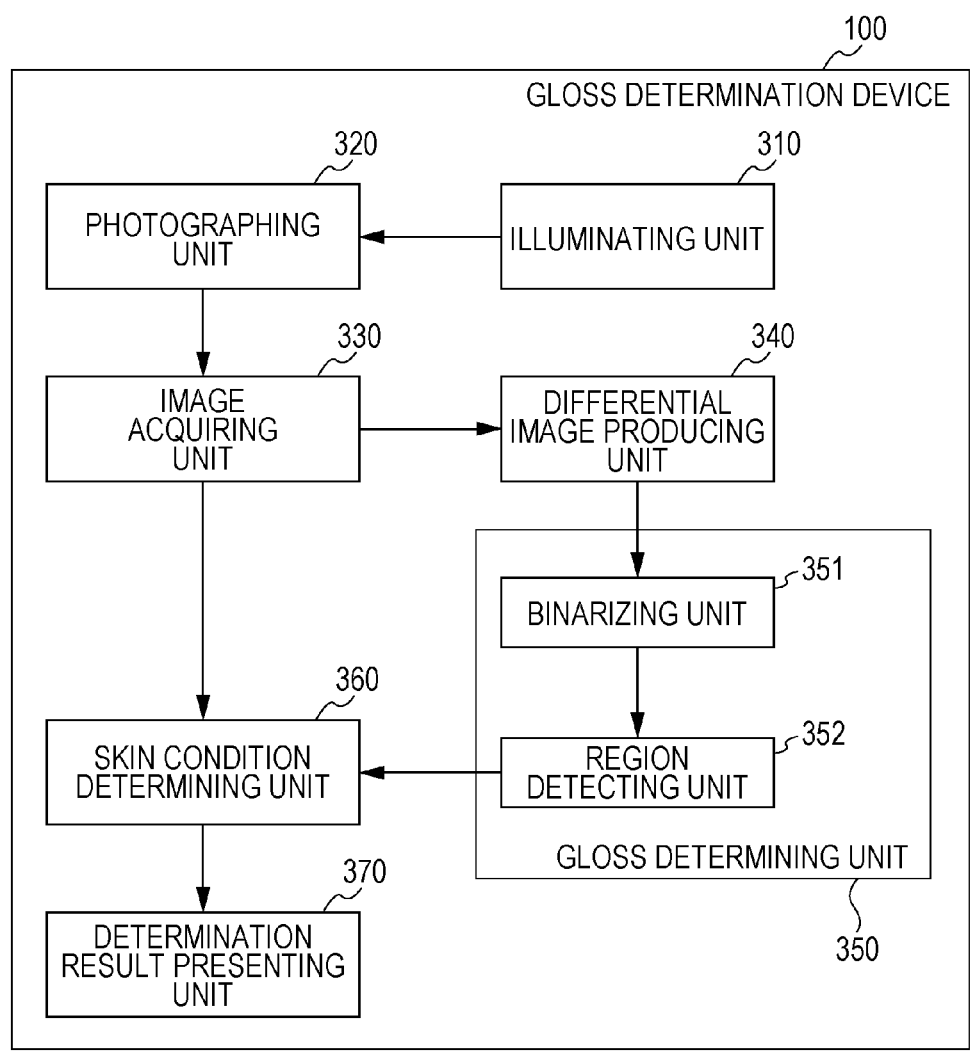
FIG. 2 illustrates an example of a configuration of the gloss determination device according to the exemplary embodiment.

FIG. 2 is a block diagram illustrating an example of a configuration of gloss determination device 100.

Referring to FIG. 2, gloss determination device 100 has illuminating unit 310, photographing unit 320, image acquiring unit 330, differential image producing unit 340, gloss determining unit 350, skin condition determining unit 360, and determination result presenting unit 370.

Illuminating unit 310 includes the above-described light 120 with a polarizing filter (see FIG. 1). In order to determine a gloss condition of face 210, illuminating unit 310 illuminates face 210, which is an object for the gloss condition determination, with polarized light, and instructs photographing unit 320 to captures images for the gloss condition determination (hereinafter referred to as "photographing for determination").

Photographing unit 320 includes the above-described camera 130 with a polarizing filter. When photographing unit 320 is instructed to perform the photographing for determination, photographing unit 320 first performs photographing by setting such that a polarized component having the same polarization direction as the polarization direction of the polarized light that illuminates face 210 (the horizontal direction in the present exemplary embodiment) is allowed to pass through the polarizing filter. Then, photographing unit 320 performs photographing by setting such that a polarized component having a polarization direction perpendicular to the polarization direction of the polarized light that illuminates face 210 (the vertical direction in the present exemplary embodiment) is allowed to pass through the polarizing filter. The above-described order of photographing may be reversed. Then, photographing unit 320 outputs the photographed two images to image acquiring unit 330.

The operations of illuminating unit 310 and photographing unit 320 may be controlled by image acquiring unit 330.

Image acquiring unit 330 acquires the two input images as a parallelly polarized image and a perpendicularly polarized image. Then, image acquiring unit 330 outputs the acquired two images to each of differential image producing unit 340 and skin condition determining unit 360. Also, image acquiring unit 330 outputs the acquired parallelly polarized image to skin condition determining unit 360.

Here, the parallelly polarized image is an image obtained by photographing face 210 illuminated by the polarized light through a polarizing filter that passes the polarized component polarized in the same direction as the polarization direction of the polarized light (the horizontal direction in the present exemplary embodiment). Also, the perpendicularly polarized image is an image obtained by photographing face 210 illuminated by the polarized light through a polarizing filter that passes the polarized component polarized in the perpendicular direction to the polarization direction of the polarized light (the vertical direction in the present exemplary embodiment).

Differential image producing unit 340 produces a differential image indicating a difference of brightness between the input parallelly polarized image and the input perpendicularly polarized image. More specifically, differential image producing unit 340 obtains a difference value by subtracting from a brightness value of a reference pixel in the parallelly polarized image a brightness value of a corresponding pixel in the perpendicularly polarized image corresponding to the reference pixel of the parallelly polarized image, and determines a pixel value of a corresponding pixel in the differential image corresponding to the reference pixel in the parallelly polarized image based on the obtained difference value. Then, differential image producing unit 340 outputs the produced differential image to gloss determining unit 350.

Gloss determining unit 350 determines a gloss condition of face 210 based on the input differential image, and outputs the determination result to skin condition determining unit 360. Gloss determining unit 350 has binarizing unit 351 and region detecting unit 352.

Binarizing unit 351 binarizes the differential image to produce a binary differential image. More specifically, bainarizing unit 351 compares each pixel value of the differential image to a predetermined threshold value (hereinafter referred to as the "binarizing threshold value"), and converts each pixel value to either a value "0" indicating that the absolute value of the brightness difference between the parallelly polarized image and the perpendicularly polarized image is small and a value "1" indicating that the absolute value of the brightness difference between the parallelly polarized image and the perpendicularly polarized image is large. Then, binarizing unit 351 outputs the produced binary differential image to region detecting unit 352.

Region detecting unit 352 detects, as a gloss region, a region in which the brightness difference between the parallelly polarized image and the perpendicularly polarized image is large (a region in which the pixel value is "1" in the present exemplary embodiment) in the input binary differential image. Then, region detecting unit 352 outputs information that indicates the detected gloss region (a result of determining a gloss condition) to skin condition determining unit 360.

Skin condition determining unit 360 detects a wrinkle by comparing the strength of each edge of a shaded part in the input parallelly polarized image to a threshold value. Then, skin condition determining unit 360 outputs to determination result presenting unit 370 information indicating a detected wrinkle region (a result of detecting a skin condition) and the input parallelly polarized image. In the gloss region indicated by the input gloss condition determination result, however, skin condition determining unit 360 sets the above-mentioned threshold value to be lower than in the other regions. In other words, skin condition determining unit 360 makes it easier to detect a wrinkle in the region in which the degree of gloss is high.

Determination result presenting unit 370 includes display 140 with a touch panel. Determination result presenting unit 370 presents to user 200 the input skin condition determination result (information regarding the skin condition). For example, determination result presenting unit 370 produces a wrinkle region image indicating a wrinkle region, and displays the wrinkle region image by superposing it on the parallelly polarized image.

Although not shown, gloss determination device 100 may have, for example, a CPU (central processing unit), a storage medium such as a ROM (read only memory) or the like having stored therein control programs, a working memory such as a RAM (random access memory) or the like, and a communications circuitry. In this case, the function of each of the above-described components may be implemented by executing the control programs by the CPU.

Gloss determination device 100 having the configuration as described above is capable of determining a gloss condition of face 210 based on differences in brightness between the parallelly polarized image and the perpendicularly polarized image, and is also capable of presenting information regarding a skin condition based on the determination result of the gloss condition.

Operation of the Device

Next, an operation of gloss determination device 100 will be described.

Figure 3:
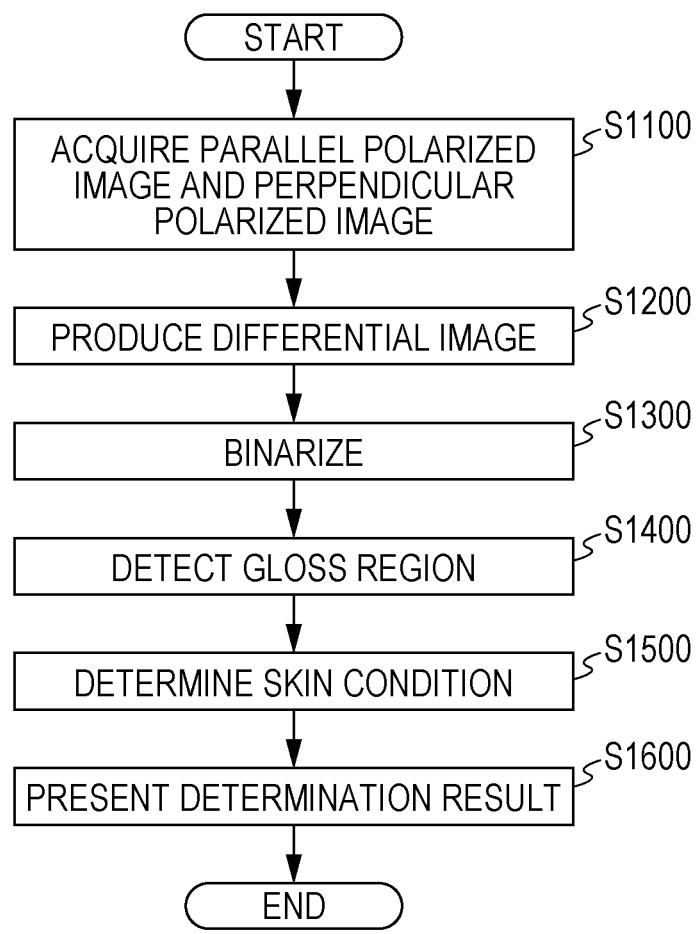
FIG. 3 is a flowchart illustrating an example of an operation of the gloss determination device according to the exemplary embodiment.

FIG. 3 is a flowchart illustrating an example of an operation of gloss determination device 100. The operation described below is started every time when a user performs a specific operation instructing to start a skin condition determination processing.

In step S1100, image acquiring unit 330 acquires a parallelly polarized image and a perpendicularly polarized image by using illuminating unit 310 and photographing unit 320.

Figure 4:
FIG. 4 shows an example of a parallelly polarized image according to the exemplary embodiment.
Figure 5:
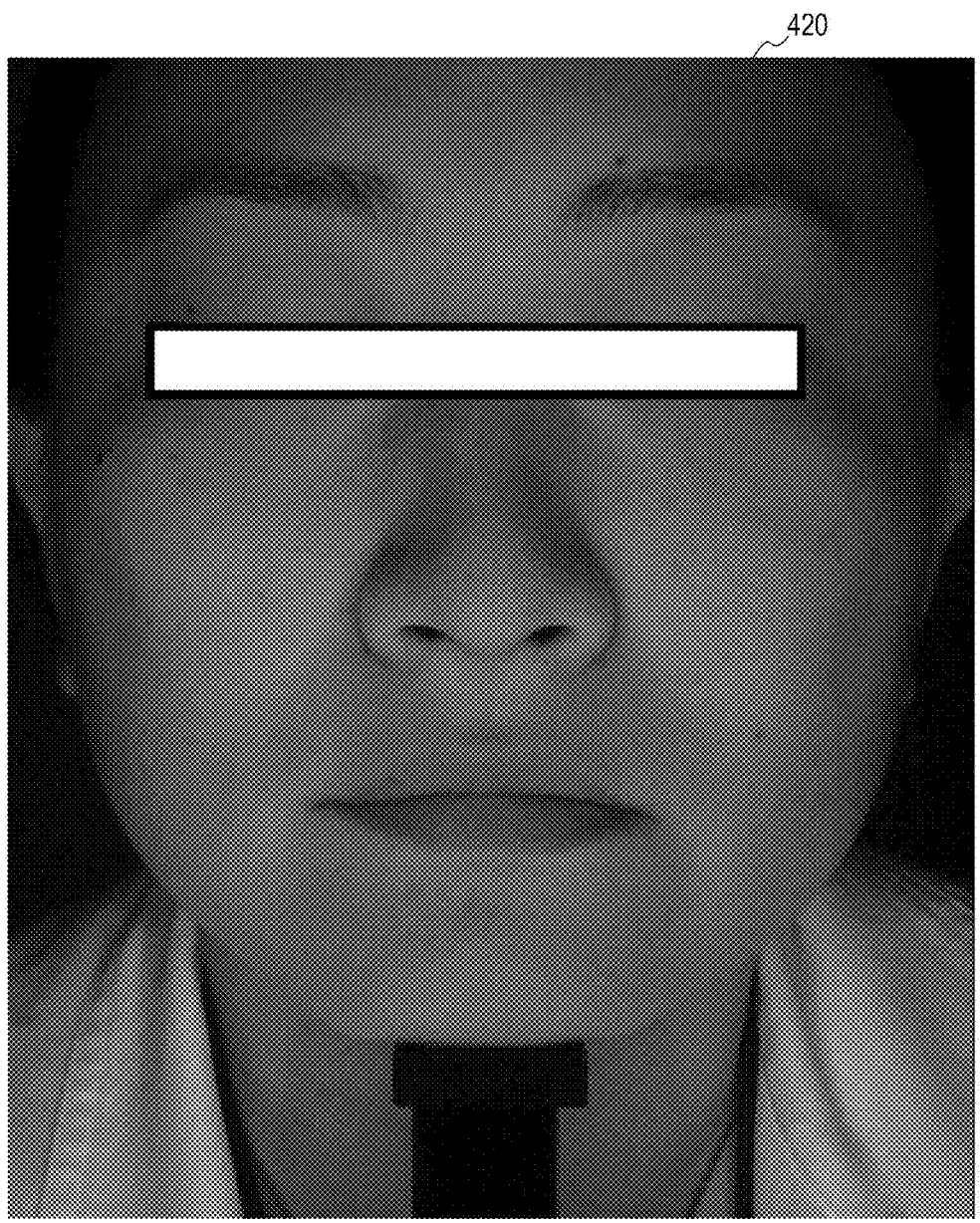
FIG. 5 shows an example of a perpendicularly polarized image according to the exemplary embodiment.

FIG. 4 shows an example of the parallelly polarized image. FIG. 5 shows an example of the perpendicularly polarized image, The parallelly polarized image is an image that has been photographed by setting such that the polarization direction of light passed through the polarizing filter of photographing unit 320 coincides with the polarization direction of the polarized light of illuminating unit 310. Accordingly, as shown in FIG. 4, parallelly polarized image 410 becomes high in brightness at parts at which specular reflection is strong.

However, the reflected light of diffuse reflection also contains a component of the same polarization direction as that of the polarized light. Further, brightness becomes high also when the skin color is bright. In addition, environment light coming from the surrounding also contains the same polarization component as the polarized light. Therefore, brightness at each part of parallelly polarized image 410 does not necessarily reflect the degree of diffuse reflection. In other words, each part of parallelly polarized image 410 becomes such a brightness that depends on the degree of specular reflection, the degree of diffuse reflection, brightness of the skin color, and the environment light.

On the other hand, the perpendicularly polarized image is an image that has been photographed by setting such that the polarization direction of light passed through the polarizing filter of photographing unit 320 is perpendicular to the polarization direction of the polarized light of illuminating unit 310. Accordingly, as shown in FIG. 5, perpendicularly polarized image 420 is less affected by specular reflection, and thus becomes such a brightness that depends only on the degree of diffuse reflection, the brightness of the skin color, and the environment light.

It is preferable that image acquiring unit 330 controls illuminating unit 310 and photographing unit 320 so that the parallelly polarized image and the perpendicularly polarized image can be captured within a time as short as possible. If the position or direction of the face is shifted, the position of each part of the face is shifted between the parallelly polarized image and the perpendicularly polarized image, so that accuracy of determining the gloss condition reduces. Incidentally, image acquiring unit 330 may detect positions of face parts such as the eye area, the edges of mouth and the like by, for example, a pattern matching from each of the parallelly polarized image and the perpendicularly polarized image, and may move, rotate, rescale, or deform the parallelly polarized image or the perpendicularly polarized image based on the detected position of face parts so that the position shift of each part of the face is reduced.

In step S1200 in FIG. 3, differential image producing unit 340 produces a differential image indicating differences in brightness between the parallelly polarized image and the perpendicularly polarized image.

Figure 6:
FIG. 6 shows an example of a differential image according to the exemplary embodiment.

FIG. 6 shows an example of the differential image. This is a differential image produced from parallelly polarized image 410 shown in FIG. 4 and perpendicularly polarized image 420 shown in FIG. 5.

As described above, brightness of each part of parallelly polarized image 410 depends on the degree of specular reflection, the degree of diffuse reflection, brightness of the skin color, and the environment light, whereas brightness of each part of perpendicularly polarized image 420 depends only on the degree of diffuse reflection, brightness of the skin color, and the environment light. Therefore, as shown in FIG. 6, differential image 430 becomes such an image that indicates only the component of specular reflection extracted from the brightness of each part of parallelly polarized image 410.

Incidentally, differential image producing unit 340 may give a predetermined weighting to each brightness value of the parallelly polarized image and the perpendicularly polarized image at the time of calculating the differential image.

In step S1300 in FIG. 3, binarizing unit 351 binarizes the differential image by using a binarizing threshold value to produce a binary differential image.

Figure 7:
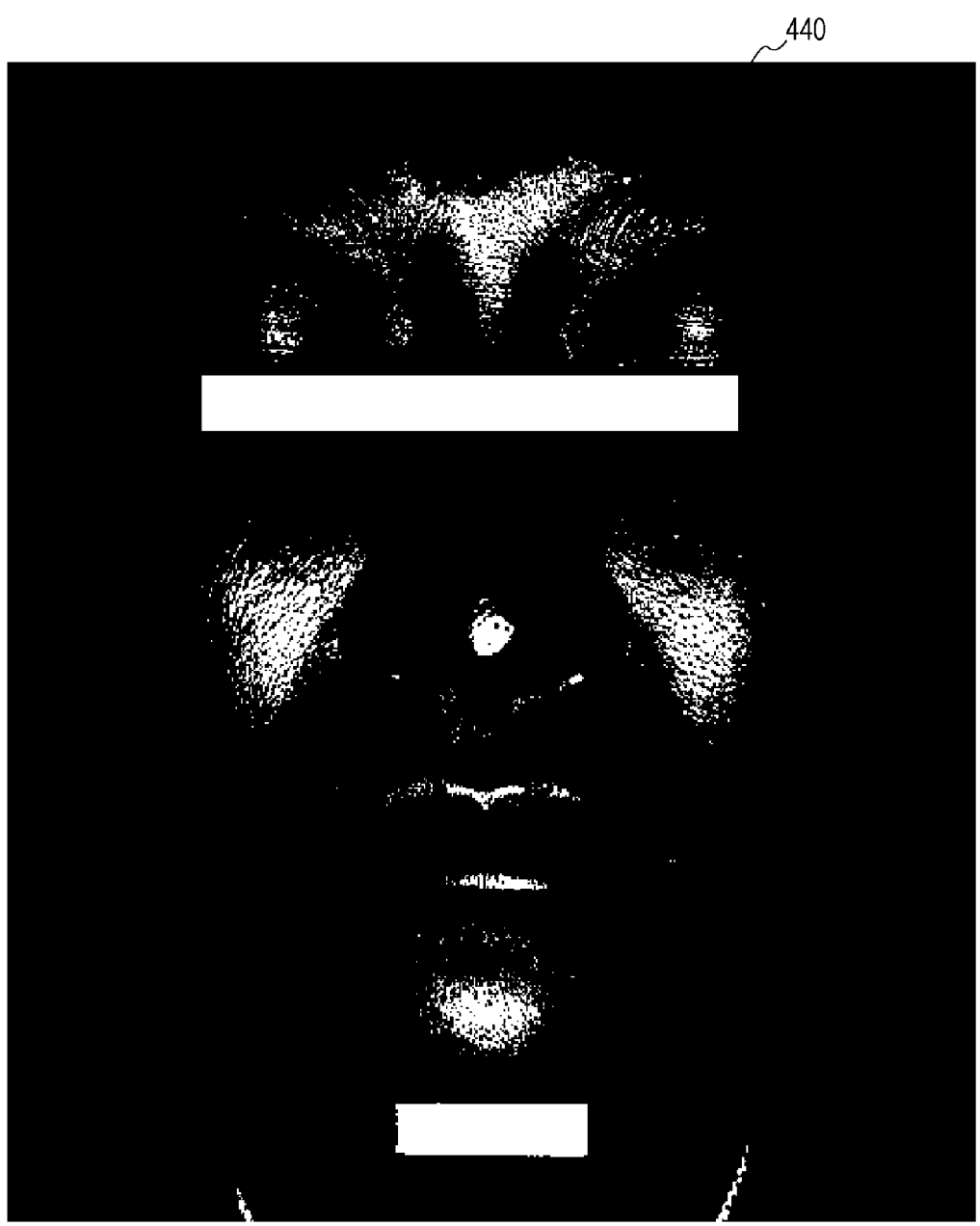
FIG. 7 shows an example of a binary differential image according to the exemplary embodiment.

FIG. 7 shows an example of the binary differential image. This is a binary differential image produced from differential image 430 shown in FIG. 6.

As shown in FIG. 7, in binary differential image 440, each pixel becomes value "1" in regions (shown as a white region in FIG. 7) in which each pixel value (brightness value) of differential image 430 is equal to or larger than the binarizing threshold value, or regions in which the brightness difference between the parallelly polarized image and the perpendicularly polarized image is large. Each pixel becomes value "0" (shown as a black region in FIG. 7) in the other regions of binary differential image 440, or regions in which the brightness difference between the parallelly polarized image and the perpendicularly polarized image is small.

In step S1400 in FIG. 3, region detecting unit 352 detects, as a gloss region, a region in which the brightness difference between the parallelly polarized image and the perpendicularly polarized image is large (a region in which each pixel value is "1" in the present exemplary embodiment) from the binary differential image.

In step S1500, skin condition determining unit 360 determines a skin condition of face 210 based on the gloss region.

Finally, in step S1600, determination result presenting unit 370 present the skin condition determination result to user 200. For example, determination result presenting unit 370 displays a determination result image in which the above-described wrinkle region image is superposed on the parallelly polarized image.

With the operation as described above, gloss determination device 100 is capable of determining a gloss condition of face 210 based on the brightness difference between the parallelly polarized image and the perpendicularly polarized image, and is further capable of presenting information regarding a skin condition based on the gloss condition determination result.

Figure 8:
FIG. 8 shows a result of binarizing a parallelly polarized image.

FIG. 8 shows a result of binarizing parallelly polarized image 410 shown in FIG. 4 for comparison. As shown in FIG. 8, it can be seen that binary parallelly polarized image 460 obtained by binarizing parallelly polarized image 410 has a larger number of regions in which the pixel values are high compared to binary differential image 440 shown in FIG. 7. This is because brightness components other than the component of specular reflection such as the component of diffuse reflection and the brightness of the skin color, are contained in binary parallelly polarized image 460 without being removed.

Advantageous Effects of the Present Exemplary Embodiment

As described above, gloss determination device 100 according to the present exemplary embodiment acquires a parallelly polarized image and a perpendicularly polarized image of face 210, produces a differential image indicating differences in brightness between the parallelly polarized image and the perpendicularly polarized image, and determines a gloss condition of face 210 based on the differential image.

Accordingly, gloss determination device 100 is capable of highly accurately extracting a component caused by specular reflection from an image obtained by photographing face 210, and is capable of accurately determining a gloss condition of face 210. Also, gloss determination device 100 is capable of performing this determination by merely photographing the two images under a single flash of illumination and image data processing. In other words, gloss determination device 100 is capable of realizing the above-described highly accurate gloss condition determination much easily compared to the conventional techniques.

Exemplary Modifications of the Present Exemplary Embodiment

A part of the components configuring gloss determination device 100 may be provided, separately from other parts, in an external device such as a server on a network. In this case, gloss determination device 100 is required to have a communication unit for communicating with such an external device.

Further, in a case that a part or all of illuminating unit 310, photographing unit 320, skin condition determining unit 360 and determination result presenting unit 370 are realized by another device, gloss determination device 100 may not necessarily have these parts. Also, in a case that gloss determination device 100 is not required to determine the gloss region, gloss determination device 100 may not have binarizing unit 351 and region detecting unit 352.

Other Exemplary Modifications

The method of acquiring the parallelly polarized image and the perpendicularly polarized image is not limited to the above-described example. For example, the gloss determination device may be configured such that the illuminating unit switches the polarization direction of the illumination light between the two polarization directions, and the photographing unit has a polarizing filter with a fixed angle to perform photographing under illumination by the illumination light of each of the two polarization directions. In this case, if the object is such a part that has a surface directed in the same direction, like a cheek of a face, the illuminating unit may be configured so as to illuminate the object with P-polarized light and S-polarized light.

Further, the gloss determination device may not present the skin condition, but may have a illumination controller that controls illumination based on a determined gloss condition so that the gloss condition becomes a desired condition. For example, the gloss determination device may have a plurality of light sources which can be individually dimmed, and may change the illumination pattern of the light sources while acquiring a gloss region under each illumination pattern. Then, the gloss determination device may perform illumination in an illumination pattern under which the area of the gloss region becomes minimum, and again photograph the face without using the polarizing filter.

Further, the gloss determination device may use the determined gloss condition to determine other various skin conditions than the wrinkle detection processing by the edge detection. For example, the gloss determination device may determine a region where the degree of gloss is high, as a region in which the degree of sebum secretion is high.

As described above, the gloss determination device is capable of improving the accuracy of various processes affected by the gloss condition or various processes for estimating conditions each having a close relation to the gloss condition, based on a highly accurately determined gloss condition.

Further, the gloss condition to be determined is not limited to the above-described example. For example, the gloss determination device may determine, as a gloss condition, the differential image itself or a representative value of pixel values in each region of the differential image. For example, the gloss determination device may detect a lip region from the photographed image, and may determine, as a gloss condition, an average of differences in brightness values between the parallelly polarized image and the perpendicularly polarized image in the detected lip region. In the case of this example, the gloss determination device can determine the degree of glossy effect of a lip balm.

Further, the gloss determination device may input other various information, and may change the binarizing threshold value depending on the input information. For example, when a measurement of the room temperature or humidity indicates an environment for skin to easily get dry, the gloss determination device may lower the binarizing threshold value to allow a gloss region to be easily detected.

Further, the polarizing directions of the polarized lights, illuminating method, photographing method, and method of presenting the skin condition determination result are not limited to the above-described examples. For example, the gloss determination device may have two cameras which are disposed closely to each other and have their respective polarizing filters that pass polarized components perpendicular to each other, and may perform simultaneous photographing using these cameras to simultaneously obtain a parallelly polarized image and a perpendicularly polarized image. Further, the gloss determination device may have another camera that captures images for other uses, separately from the camera that captures the parallelly polarized image and the perpendicularly polarized image.

Further, the object having a gloss condition to be determined is not limited to the human face. For example, the gloss determination device may be used to determine a gloss condition of an industrial product.

Summary of the Present Disclosure

A gloss determination device of the present disclosure comprises: an image acquiring unit that acquires a parallelly polarized image obtained by photographing an object illuminated by first polarized light through a polarizing filter which passes a polarized component polarized in a same direction as a polarization direction of the first polarized light and a perpendicularly polarized image obtained by photographing the object illuminated by second polarized light through a polarizing filter which passes a polarized component polarized in a perpendicular direction to the polarization direction of the second polarized light; a differential image producing unit that produces a differential image indicating differences in brightness between the parallelly polarized image and the perpendicularly polarized image; and a gloss determining unit that determines a gloss condition of the object based on the differential image.

In the above gloss determination device, the differential image producing unit may obtain a difference value by subtracting from a brightness value of a reference pixel in the parallelly polarized image a brightness value of a corresponding pixel in the perpendicularly polarized image corresponding to the reference pixel in the parallelly polarized image, and determine a pixel value of a corresponding pixel in the differential image corresponding to the reference pixel in the parallelly polarized image based on the obtained difference value. In this case, the gloss determining unit may have a binarizing unit that binarizes the differential image to produce a binary differential image, and a region detecting unit that detects a high gloss region in which the degree of gloss is high on the object based on the binary differential image.

Further, in the above gloss determination device, the binarizing unit may adjust a threshold value for producing the binary differential image so that the gloss region satisfies a predetermined condition.

Further, in the above gloss determination device, the first polarized light used to capture the parallelly polarized image and the second polarized light used to capture the perpendicularly polarized image may illuminate the object from a same position, and the parallelly polarized image and the perpendicularly polarized image may be obtained by photographing the object from a same position.

Further, in the above gloss determination device, the object may be a skin of a human, and the gloss determination device may further have a skin condition determining unit that determines a condition of the skin based on the gloss condition and an image obtained by photographing the object from the same position as the position from which the parallelly polarized image and the perpendicularly polarized image have been captured, and a determination result presenting unit that presents information regarding the determined condition of the skin.

Further, the gloss determination device may further have an illumination controller that controls, based on the gloss condition, illumination that is used when the object is photographed from the same position as the position from which the parallelly polarized image and the perpendicularly polarized image have been captured.

A gloss determination method of the present disclosure comprises the steps of: acquiring a parallelly polarized image obtained by photographing an object illuminated by first polarized light through a polarizing filter which passes a polarized component polarized in a same direction as a polarization direction of the first polarized light and a perpendicularly polarized image obtained by photographing the object illuminated by second polarized light through a polarizing filter which passes a polarized component polarized in a perpendicular direction to the polarization direction of the second polarized light; producing a differential image indicating differences in brightness between the parallelly polarized image and the perpendicularly polarized image; and determining a gloss condition of the object based on the differential image.

Although an example of implementing the present disclosure by hardware has been described in the above-described exemplary embodiment, the present disclosure may be implemented by software in conjunction with hardware.

Each of the functional blocks used for describing the above exemplary embodiment may typically be implemented as an LSI (Large Scale Integration), which is an integrated circuit. These functional blocks may be individually mounted on separate chips, or a part or all of the functional blocks may be mounted on a single chip. The functional blocks may be integrated as an LSI, or as a so-called IC (Integrated Circuit), system LSI, super LSI, or ultra LSI, depending on the degree of integration.

The present disclosure is applicable to a gloss determination device and a gloss determination method that is capable of easily and accurately determining a gloss condition of an object.

What is claimed is:

1. A gloss determination device comprising:
   image acquiring circuitry that, in operation, acquires a parallelly polarized image captured by photographing an object illuminated by first polarized light, through a polarizing filter which passes a polarized component polarized in a same direction as a polarization direction of the first polarized light, and a perpendicularly polarized image captured by photographing the object illuminated by second polarized light having a same polarized direction as the first polarized light, through a polarizing filter which passes a polarized component polarized in a perpendicular direction to the polarization direction of the second polarized light;
   differential image producing circuitry that, in operation, produces a differential image indicating differences in brightness between the parallelly polarized image and the perpendicularly polarized image; and
   gloss determining circuitry that, in operation, determines a gloss condition of the object based on the differential image.

2. The gloss determination device according to claim 1, wherein the differential image producing circuitry obtains a difference value by subtracting, from a brightness value of a reference pixel in the parallelly polarized image, a brightness value of a first corresponding pixel in the perpendicularly polarized image corresponding to the reference pixel in the parallelly polarized image, and determines a pixel value of a second corresponding pixel in the differential image corresponding to the reference pixel in the parallelly polarized image based on the obtained difference value, and
wherein the gloss determining circuitry includes:
   binarizing circuitry that, in operation, binarizes the differential image to produce a binary differential image; and
   region detecting circuitry that, in operation, detects a high gloss region in which a degree of gloss is higher than a threshold value on the object based on the binary differential image.

3. The gloss determination device according to claim 2, wherein the binarizing circuitry adjusts the threshold value for producing the binary differential image, the adjustment resulting in the gloss region satisfying a predetermined condition.

4. The gloss determination device according to claim 1, wherein the first polarized light and the second polarized light illuminate the object from a same position, and
wherein the parallelly polarized image and the perpendicularly polarized image are captured by photographing the object from a same position.

5. The gloss determination device according to claim 4, wherein the object is a skin of a human, and
wherein the gloss determination device further comprises:
   skin condition determining circuitry that, in operation, determines a condition of the skin based on the gloss condition and an image captured by photographing the object from the same position as the position from which the parallelly polarized image and the perpendicularly polarized image have been captured; and
   determination result output circuitry that, in operation, outputs information regarding the determined condition of the skin.

6. The gloss determination device according to claim 4, further comprising an illumination controller that controls, based on the gloss condition, illumination to the object, the illumination being used when the object is photographed from the same position as the position from which the parallelly polarized image and the perpendicularly polarized image have been captured.

7. A gloss determination method comprising the steps of:
   acquiring a parallelly polarized image captured by photographing an object illuminated by first polarized light, through a polarizing filter which passes a polarized component polarized in a same direction as a polarization direction of the first polarized light and a perpendicularly polarized image captured by photographing the object illuminated by second polarized light having a same polarized direction as the first polarized light, through a polarizing filter which passes a polarized component polarized in a perpendicular direction to the polarization direction of the second polarized light;
   producing a differential image indicating differences in brightness between the parallelly polarized image and the perpendicularly polarized image; and
   determining a gloss condition of the object based on the differential image.

* * * * *